(12) United States Patent
Kammerer

(10) Patent No.: US 8,047,982 B2
(45) Date of Patent: Nov. 1, 2011

(54) MESH TAPE WITH WING-LIKE EXTENSIONS FOR TREATING FEMALE URINARY INCONTINENCE

(75) Inventor: Gene W. Kammerer, East Brunswick, NJ (US)

(73) Assignee: Ethicon, Inc., Somerville, NJ (US)

( * ) Notice: Subject to any disclaimer, the term of this patent is extended or adjusted under 35 U.S.C. 154(b) by 783 days.

(21) Appl. No.: 10/854,289

(22) Filed: May 7, 2004

(65) Prior Publication Data
US 2005/0250978 A1  Nov. 10, 2005

(51) Int. Cl.
*A61F 2/00* (2006.01)
(52) U.S. Cl. ............................. 600/37; 600/30
(58) Field of Classification Search ............... 600/29–31, 600/37, 205, 201, 210; 606/151; 623/4.1, 623/23.64, 23.66
See application file for complete search history.

(56) References Cited

U.S. PATENT DOCUMENTS

| | | |
|---|---|---|
| 3,182,662 A | 5/1965 | Shirodkar |
| 3,212,502 A | 10/1965 | Myers |
| 3,311,110 A | 3/1967 | Singman |
| 3,372,695 A | 3/1968 | Beliveau et al. |
| 3,472,232 A | 10/1969 | Earl |
| 3,608,095 A | 9/1971 | Barry |
| 3,763,860 A | 10/1973 | Clarke |
| 3,858,783 A | 1/1975 | Kapitanov et al. |
| 3,924,633 A | 12/1975 | Cook et al. |
| 4,037,603 A | 7/1977 | Wendorff |
| 4,128,100 A | 12/1978 | Wendorff |
| 4,235,238 A | 11/1980 | Ogiu et al. |
| 4,392,495 A | 7/1983 | Bayers |
| 4,441,497 A | 4/1984 | Paudler |
| 4,509,516 A | 4/1985 | Richmond |
| 4,549,545 A | 10/1985 | Levy |
| 4,655,221 A | 4/1987 | Devereux |
| 4,946,467 A | 8/1990 | Ohi et al. |
| 5,013,292 A | 5/1991 | Lemay |
| 5,032,508 A | 7/1991 | Naughton et al. |
| 5,080,667 A | 1/1992 | Chen et al. |
| 5,112,344 A | 5/1992 | Petros |
| 5,180,385 A | 1/1993 | Sontag |
| 5,250,033 A | 10/1993 | Evans et al. |

(Continued)

FOREIGN PATENT DOCUMENTS

AU    B278089    9/1967

(Continued)

OTHER PUBLICATIONS

Petros, P.E. Papa, "Vault Prolapse II: Restoration of Dynamic Vaginal Supports by Infracoccygeal Sacropex, an Axial Day-Case Vaginal Procedure", International Urogynecol Journal, Springer-Verlag London Ltd., 2001, vol. 12, pp. 263-303.
Petros, P.E. Papa, "Vault Prolapse I: Dynamic Supports of the Vagina", Internation Urogynecol Journel, Springer-Vergag London Ltd., 2001, vol. 12, pp. 292-295.
Petros, P.E. Papa, "An Integral Theory for the Diagnosis and Management of Female Urinary Incontinence", Scandinavian Journal of Urology and Nephrology, Supplement 153: 1993.

(Continued)

*Primary Examiner* — Charles A Marmor, II
*Assistant Examiner* — Christine D Hopkins

(57) ABSTRACT

A urethra support having an elongated mesh tape portion and a mesh extension affixed to the tape portion transverse thereto. In accordance with a method of the invention, the urethra support is inserted into the lower pelvic cavity of a patient with the tape portion forming a sling extending beneath and supporting the urethra of the patient. In this position, the tape portion is generally perpendicular to the urethra. The extension is inserted into the peri-urethral fascia along at least a portion of the length of the urethra. This induces the formation of scar tissue proximate the extension, with the scar tissue eventually contracting thereby compressing the urethra.

18 Claims, 5 Drawing Sheets

U.S. PATENT DOCUMENTS

| | | | |
|---|---|---|---|
| 5,281,237 A | 1/1994 | Gimpelson | |
| 5,337,736 A | 8/1994 | Reddy | |
| 5,362,294 A | 11/1994 | Seitzinger | |
| 5,368,595 A | 11/1994 | Lewis | |
| 5,368,756 A | 11/1994 | Vogel et al. | |
| 5,382,257 A | 1/1995 | Lewis et al. | |
| 5,383,904 A | 1/1995 | Totakura et al. | |
| 5,403,328 A | 4/1995 | Shallman | |
| 5,441,508 A | 8/1995 | Gazielly et al. | |
| 5,450,860 A | 9/1995 | O'Connor | |
| 5,480,436 A | 1/1996 | Bakker et al. | |
| 5,507,796 A | 4/1996 | Hasson | |
| 5,582,188 A | 12/1996 | Benderev | |
| 5,611,515 A | 3/1997 | Benderev et al. | |
| 5,628,756 A | 5/1997 | Barker, Jr. et al. | |
| 5,645,568 A | 7/1997 | Chervitz et al. | |
| 5,741,299 A | 4/1998 | Rudt | |
| 5,816,258 A | 10/1998 | Jervis | |
| 5,836,315 A | 11/1998 | Benderev et al. | |
| 5,840,011 A | 11/1998 | Landgrebe et al. | |
| 5,855,549 A | 1/1999 | Newman | |
| 5,860,425 A | 1/1999 | Benderev et al. | |
| 5,899,909 A | 5/1999 | Claren et al. | |
| 5,899,999 A | 5/1999 | De Bonet | |
| 5,922,026 A | 7/1999 | Chin | |
| 5,934,283 A | 8/1999 | Willem et al. | |
| 5,935,122 A | 8/1999 | Fourkas et al. | |
| 5,945,122 A | 8/1999 | Abra et al. | |
| 5,997,554 A | 12/1999 | Thompson | |
| 6,010,447 A | 1/2000 | Kardjian | |
| 6,030,393 A | 2/2000 | Corlew | |
| 6,042,534 A | 3/2000 | Gellman et al. | |
| 6,110,101 A | 8/2000 | Tihon et al. | |
| 6,117,067 A | 9/2000 | Gil-Vernet | |
| 6,197,036 B1 | 3/2001 | Tripp et al. | |
| 6,221,005 B1 | 4/2001 | Bruckner et al. | |
| 6,273,852 B1 | 8/2001 | Lehe et al. | |
| 6,306,079 B1 | 10/2001 | Trabucco | |
| 6,334,446 B1 | 1/2002 | Beyar | |
| 6,382,214 B1 | 5/2002 | Raz et al. | |
| 6,406,423 B1 | 6/2002 | Scetbon | |
| 6,475,139 B1 | 11/2002 | Miller | |
| 6,491,703 B1 | 12/2002 | Ulmsten | |
| 6,575,897 B1 * | 6/2003 | Ory et al. | 600/30 |
| 6,605,097 B1 | 8/2003 | Lehe et al. | |
| 6,612,977 B2 | 9/2003 | Staskin et al. | |
| 6,691,711 B2 | 2/2004 | Raz et al. | |
| 6,808,486 B1 * | 10/2004 | O'Donnell | 600/30 |
| 7,070,558 B2 * | 7/2006 | Gellman et al. | 600/30 |
| 7,179,224 B2 * | 2/2007 | Willis | 600/205 |
| 2001/0018549 A1 | 8/2001 | Scetbon | |
| 2001/0049467 A1 | 12/2001 | Lehe et al. | |
| 2002/0028980 A1 | 3/2002 | Thierfelder et al. | |
| 2002/0058959 A1 | 5/2002 | Gellman | |
| 2002/0077526 A1 | 6/2002 | Kammerer et al. | |
| 2002/0091373 A1 | 7/2002 | Berger | |
| 2002/0183588 A1 | 12/2002 | Fierro | |
| 2002/0188169 A1 | 12/2002 | Kammerer et al. | |
| 2003/0004395 A1 | 1/2003 | Therin | |
| 2003/0023138 A1 | 1/2003 | Luscombe | |
| 2003/0069469 A1 * | 4/2003 | Li | 600/30 |
| 2003/0100954 A1 | 5/2003 | Schuldt-Hempe et al. | |
| 2003/0149440 A1 | 8/2003 | Kammerer et al. | |
| 2003/0176762 A1 | 9/2003 | Kammerer | |
| 2003/0195386 A1 | 10/2003 | Thierfelder et al. | |
| 2003/0220538 A1 | 11/2003 | Jacquetin | |
| 2004/0039453 A1 | 2/2004 | Anderson et al. | |
| 2005/0240075 A1 * | 10/2005 | Li | 600/30 |
| 2005/0245787 A1 * | 11/2005 | Cox et al. | 600/37 |

FOREIGN PATENT DOCUMENTS

| | | |
|---|---|---|
| AU | B441561 | 10/1973 |
| DE | 3223153 C1 | 8/1983 |
| DE | 42 20 283 A1 | 12/1993 |
| DE | 4334419 | 4/1995 |
| EP | 0598976 | 6/1994 |
| EP | 0668056 A1 | 8/1995 |
| EP | 0 774 240 A1 | 5/1997 |
| EP | 0941712 | 9/1999 |
| EP | 1025811 | 8/2000 |
| EP | 1 238 638 A | 9/2002 |
| SE | 503271 | 4/1996 |
| WO | 9003766 | 4/1990 |
| WO | 9606567 | 3/1996 |
| WO | 9713465 | 4/1997 |
| WO | 9831301 | 7/1998 |
| WO | WO 98/35632 A | 8/1998 |
| WO | WO 01/06951 A1 | 2/2001 |
| WO | WO 01/39670 A1 | 6/2001 |
| WO | WO 02/19944 A2 | 3/2002 |
| WO | WO 02/28312 A1 | 4/2002 |
| WO | 0238079 | 5/2002 |
| WO | WO 03/092546 A | 11/2003 |
| WO | WO 2004/012626 A1 | 2/2004 |
| WO | WO 2004/067056 A | 8/2004 |

OTHER PUBLICATIONS

"TVT Tension-free Vaginal Tape, Minimally Invasive Highly Effective Treatment for Female Stress Urinary Incontinence", Gynecare, Ethicon, Inc., 1999, pp. 1-6.

"AMS Sparc Sling System", American Medical Systems, Inc., Minnetonka, MN, 2001, pp. 1-6.

Co-pending appln. "Apparatus and Method for Treating Female Incontinence", U.S. Appl. No. 09/691,359, filed Oct. 18, 2000, Inventor Jom Lehe, et al.

Co-pending appln. "Surgical Instrument and Method for Treating Female Urinary Incontinence", U.S. Appl. No. 09/716,546, filed Nov. 20, 2000, Inventor. Ulf Umstead, et al.

Co-pending appln. "Method and Apparatus for adjusting Flexible Areal Polymer Implants", U.S. Appl. No. 09/589,242, filed Jun. 7, 2000, Inventor Jorg Priewe, et al.

Co-pending appln. "Surgical Instrument and Method for Treating Organ Prolapse Conditions", U.S. Appl. No. 10/359,406, filed Feb. 6, 2003, Inventor: Gene W. Kammerer (with replacement drawings).

Co-pending appln. "Surgical Instrument and Method for Treating Female Urinary Incontinence", U.S. Appl. No. 60/356,697, filed Feb. 14, 2002, Inventor Gene W. Kammerer.

"Surgical Instrument and Method for Treating Female Urinary Incontinence", U.S. Appl. No. 10/285,281, filed Oct. 21, 2002, Inventor: Kammerer et al.

Giberti, "Transvaginal Sacrospinous Colpopexy by Palpation—A New Minimally Invasive Procedure Using an Anchoring System", Urology, (2001) pp. 666-668, vol. 57.

Cosson et al., "Cystocele Repair by Vaginal Patch", Progres En Urologie, (2001) pp. 340-346, vol. 11.

Collinet et al., "The Vaginal Patch Cure of Cystocele", J. Gynecol. Obstet. Biol. Reprod., (2000) pp. 197-201, vol. 29, No. 2.

Leanza et al., "New Technique for Correcting Both Incontinence and Cystocele: T.I.C.T.", Urogynaecologia International Journal (2001) pp. 133-140, vol. 15, No. 3.

International Search Report dated Nov. 10, 2005, for corresponding international application PCt/US2005/014576.

Written Opinion dated Nov. 8, 2005, for corresponding International Application No. PCT/US2005/014576.

U.S. Application "Mesh for Pelvic Floor Repair" U.S. Appl. No. 10/263,933, filed Oct. 3, 2002, Inventor: Ulf Ulmsten et al.

Giberti, "Transvaginal Sacrospinous Colpopexy by Palpation-A New Minimally Invasive Procedure Using an Anchoring System", Urology, (2001) pp. 666-668, vol. 57.

Cosson et al., "Cystocele Repair by Vaginal Patch", Progres En Urologie, (2001) pp. 340-346, vol. 11.

Collinet et al., "The Vaginal Patch Cure of Cystocele", J. Gynecol. Obstet. Biol. Reprod., (2000) pp. 197-201, vol. 29, No. 2.

Leanza et al., "New Technique for Correcting Both Incontinence and Cystocele: T.I.C.T.", Urogynaecologia International Journal (2001) pp. 133-140, vol. 15, No. 3.

* cited by examiner

MESH TAPE WITH WING-LIKE EXTENSIONS FOR TREATING FEMALE URINARY INCONTINENCE

FIELD OF THE INVENTION

The present invention relates to surgical mesh tape that is implantable into the lower pelvic cavity of a female to provide support to the urethra, and more particularly to a tape having an increased area of contact to provide greater support.

BACKGROUND OF THE INVENTION

Numerous women suffer from Stress Urinary Incontinence (SUI), caused by childbirth, loss of pelvic muscle tone, intrinsic sphincter deficiency (ISD) and/or estrogen loss. SUI and ISD lead to inadvertent loss of urine due to activities such as laughing, coughing, sneezing or exercising. Various treatments and appliances have been proposed to address this problem, including methods and apparatus to create pressure on the sphincter, such as implantable balloon devices. This type of surgery is traumatic and sometimes results in damage to the nerves around the bladder neck attributable to the magnitude of dissection required. Further, implantable balloons tend to erode tissue with which they are in contact. Bulking agents that are injected into the layers of the urethra have also been used, however, these agents usually dissipate over time, in some cases migrate to other parts of the body away from the site of implantation, and the problem eventually returns.

Surgical tape for supporting the female urethra to treat urinary incontinence has been successfully employed. For example, U.S. Pat. No. 6,273,852 discloses methods and apparatus for implanting surgical tape for supporting the urethra to address incontinence. U.S. Pat. No. 6,273,852 is owned by the present assignee and is incorporated herein by reference. Surgical tape and implantation systems for treating SUI are also available commercially from the assignee herein, e.g., under the trademark TVT™ tension free support for incontinence, sold by GYNECARE WORLDWIDE, a division of the present assignee.

In the use of a simple band of tape placed under the urethra, the action of treatment is the providing of a backstop to the urethra, over which the urethra will bend or against which it will compress. This treatment primarily addresses a condition known as hypermobility in stress urinary incontinence. This action essentially decreases the internal diameter of the urethra, thereby requiring a higher pressure within the bladder to overcome the closure mechanism of the urethra. To some degree, the intrinsic weakness of the urethral sphincter is enhanced by the placement of this type tape sling as well. However, there are many patients in which this treatment is not significantly effective to correct ISD. This is true particularly in women with severe ISD, in which the sphincter is significantly weakened and hypermobility is not present or mildly present. Severe ISD is diagnosed by urodynamic measurements of the opening or closing pressure of the urethra. In normal female patients, this pressure is approximately 60 cm of H2O to 120 cm of H2O. In a female patient who has a urethral sphincter dysfunction, it can be as low as 20 cm of H2O and the patient can still maintain some normal urine retention. In the worst cases, ISD in patients can be diagnosed by urethral closing pressures below 20 cm H2O. Notwithstanding known apparatus and techniques, alternative apparatus and methods are always of interest to provide results different from those of known methods, which, in certain instances and applications, may be preferable to known methods.

SUMMARY OF THE INVENTION

The limitations of prior art devices for aiding in the treatment of urinary incontinence are addressed by the present invention, which includes a urethra support having an elongated mesh tape portion and a mesh extension affixed to the tape portion transverse to the tape portion. In accordance with a method of the invention, a urethra support of the foregoing type is inserted into the lower pelvic cavity of a patient with the tape portion forming a sling extending beneath and supporting the urethra of the patient. In this position, the tape portion is generally perpendicular to the urethra. The extension is inserted into the peri-urethral fascia along at least a portion of the length of the urethra, inducing the formation of scar tissue that compresses the urethra.

BRIEF DESCRIPTION OF THE FIGURES

For a better understanding of the present invention, reference is made to the following detailed description of various exemplary embodiments considered in conjunction with the accompanying drawings.

DETAILED DESCRIPTION OF THE INVENTION

Figure 1:
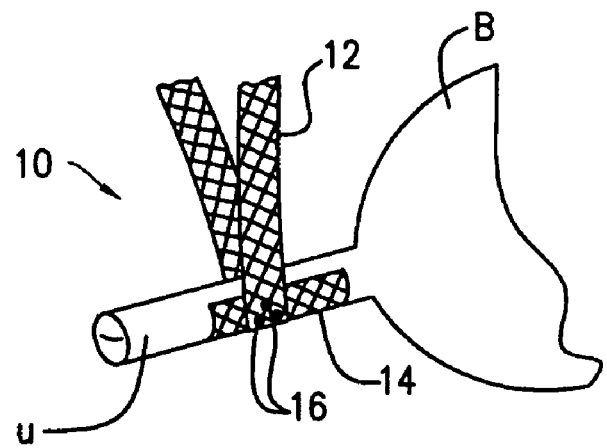
FIG. 1 is a diagrammatic view of a urethra support in accordance with an exemplary embodiment of the present invention supporting the urethra of a patient.

FIG. 1 shows a urethra support 10 extending under and supporting the urethra U of a patient proximate to the patient's bladder B. The urethra support 10 is generally in the form of an elongated tape made from a surgical mesh material, such as PROLENE® Mesh manufactured by Ethicon of Somerville, N.J. The composition of the urethra support 10, as well as the methodology used for its placement in the body of a patient, are described at length in U.S. Pat. Nos. 6,273,852 and 5,112,344, both of which are incorporated by reference herein. The urethra support 10 has an elongated tape portion 12 which loops under the urethra U, extends over the pubis and through the abdominal wall, as described in U.S. Pat. No. 6,273,852. Alternatively, the tape portion 12 can exit through the obturator foramen OF of the pelvic bone Pb as disclosed in the instructions for use of the GYNECARE TVT* Obturator System Tension-free Support for Incontinence (see FIG. 6). In the present invention, an extension panel 14 is attached to the tape portion 12 via adhesive, interweaving or spot welding, e.g., at points 16. When used as a support sling for the urethra U, the tape portion 12 crosses under the urethra U generally perpendicularly thereto. The extension 14 increases the contact area of the urethra support 10 with the urethra U along its length, i.e., parallel thereto. The extension 14 preferably assumes a U-shaped trough configuration when positioned under the urethra U, enclosing the lateral and inferior aspects of the urethra U and increasing the contact area between the urethra support 10 and the urethra U. Minimum dissection is required for the insertion of the urethra support 10 (only slightly more than that required for the tape portion 12). If the extension 14 is a separate panel joined to the tape portion 12, it can be placed either above or below the tape portion 12 relative to the urethra U and can extend beyond the tape portion 12 parallel to the urethra to a selected amount in one or both directions. The length and width of the extension 14 can be adjusted by trimming with a scissor or scalpel prior to insertion into the body, thereby customizing the urethra support 10 for placement in a specific patient. In use, the extension 14 is preferably placed within the peri-urethral fascia along the length of the urethra U. The extension 14 wraps around the urethra U, e.g., wrapping about 180°, 235° or 395° (overlapping itself) The in-growth of scar tissue into the mesh of the tape portion 12 and extension 14 creates a dense layer of tissue which contracts and creates an inwardly directed pressure compressing the urethra sheath and aiding in the closure of the urethra to prevent the inadvertent escape of urine.

Figure 2:
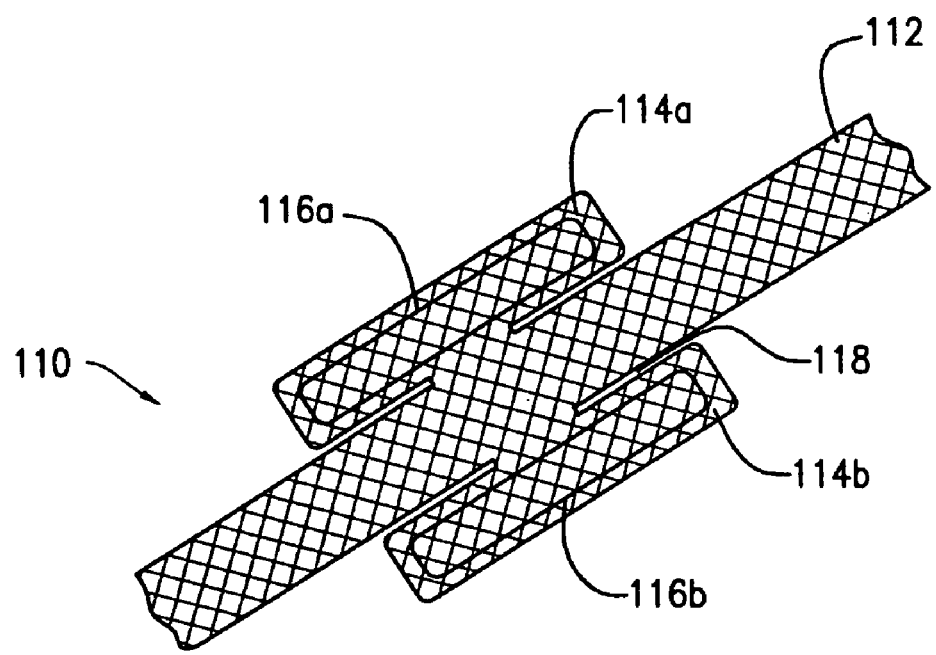
FIG. 2 is a plan view of a urethra support in accordance with a second embodiment of the present invention.

FIG. 2 shows a urethra support 110 in accordance with an alternative embodiment of the present invention. More particularly, the urethra support 110 has extensions 114a, 114b, which are integrally formed with the tape portion 112. The extensions 114a, 114b may be cut out of a sheet of mesh material, e.g., by a cutting die or a laser. The urethra support 10, 110 may be biased to a position, which is similar to that of the urethra support 10 as shown in FIG. 1 (i.e., with the extensions 14, 114a, 114b approximating the shape of the urethra) by subjecting it to heated dies. Alternatively, a shaping element or elements 116a, 116b may be incorporated into the urethra support 110 that induce the urethra support 110 to retain and/or assume a predetermined shape configuration, e.g., embracing the urethra U. The shaping element(s) 116a, 116b may be made from a material that retains a configuration after placement of the urethra support 110, i.e., like a bendable, deformable wire. Alternatively, the shaping element(s) 116a, 116b may be formed of a resilient material that can be flattened to allow placement of the urethra support 110 and then automatically assume a predetermined shaped configuration after placement due to elastic or shape memory. The shaping element(s) 116a, 116b may be attached to the urethra support 110 by tethers or stitches, may be enclosed between layers of the material of which the urethra support 110 is composed, may be interwoven into the material of the urethra support 110, may be glued or otherwise affixed to the urethra support 110, or may be a direct extension of the urethra support tape 110. The extensions 114a, 114b may be partially separated from the tape portion 112 by slits 118 to allow the extensions 114a, 114b to conform more readily to the urethra U.

Figure 3:
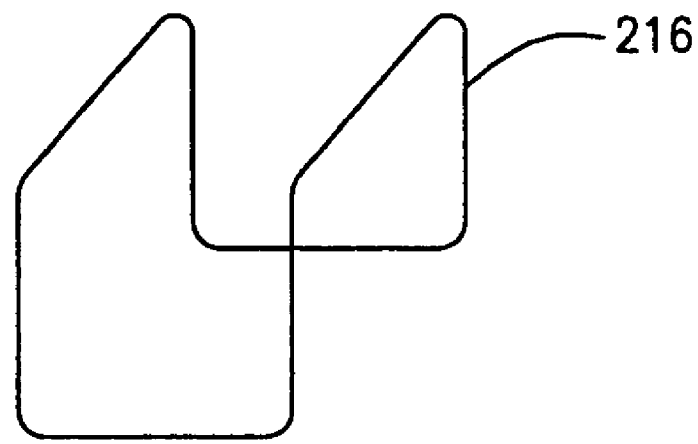
FIG. 3 is a perspective view of a urethra support in accordance with a third embodiment of the present invention.

FIG. 3 shows a resilient shaping element 216 that has a trough-shaped, relaxed configuration that could be utilized to cause a urethra support, e.g., 110 to wrap itself around the urethra U of a patient after placement in proximity thereto. More particularly, the shaping element 216 may be flattened under tension to assume the appropriate configuration of shaping elements 116a, 116b of FIG. 2, allowing the placement of the urethra support 110. After the urethra support 110 is implanted, the constraints holding it in a flattened configuration are removed, whereupon the shaping element 216 elastically returns to the shape shown in FIG. 3, thus urging an associated extension, e.g. 114a into a configuration embracing the urethra U. The shaping element 216 may be formed from a heat-set polypropylene suture or a Nitinol wire with a preset shape.

Figure 4:
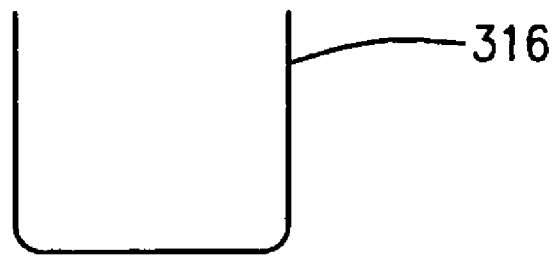
FIG. 4 is a plan view of a urethra support in accordance with a fourth embodiment of the present invention.

FIG. 4 illustrates yet another form of resilient shaping element 316, viz., in the form of a single resilient strand, of e.g., Nitinol or preset polypropylene with a "U"-shape.

Figure 5:
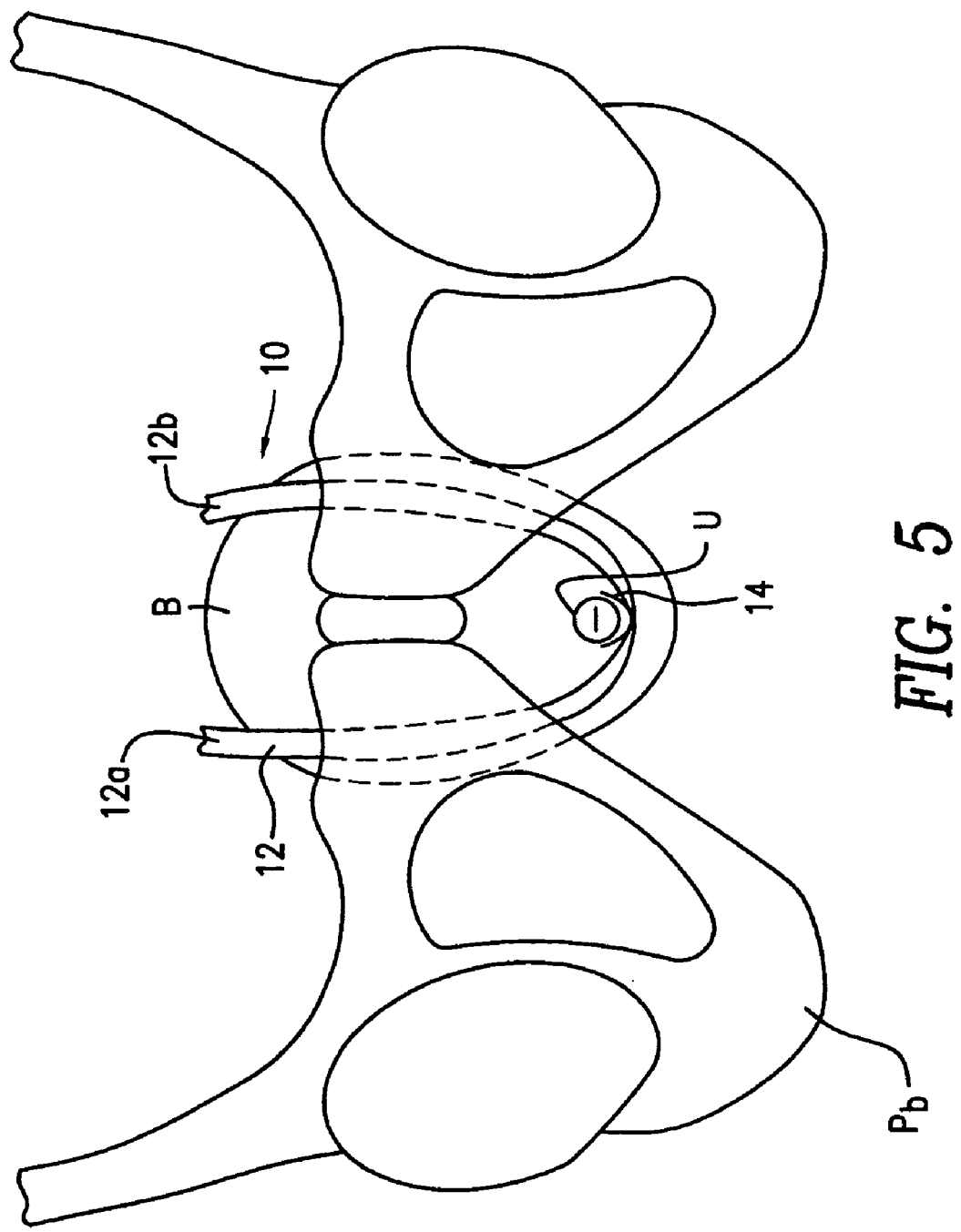
FIG. 5 is a front view of the pelvic bone of a female showing the position of the support tape of the urethra with a retro-pubic passage of the tape.

FIG. 5 illustrates the placement of the urethra support 10 with the tape portion 12 under the urethra U and with a retro-pubic passage of the tape ends, 12a and 12b.

Figure 6:
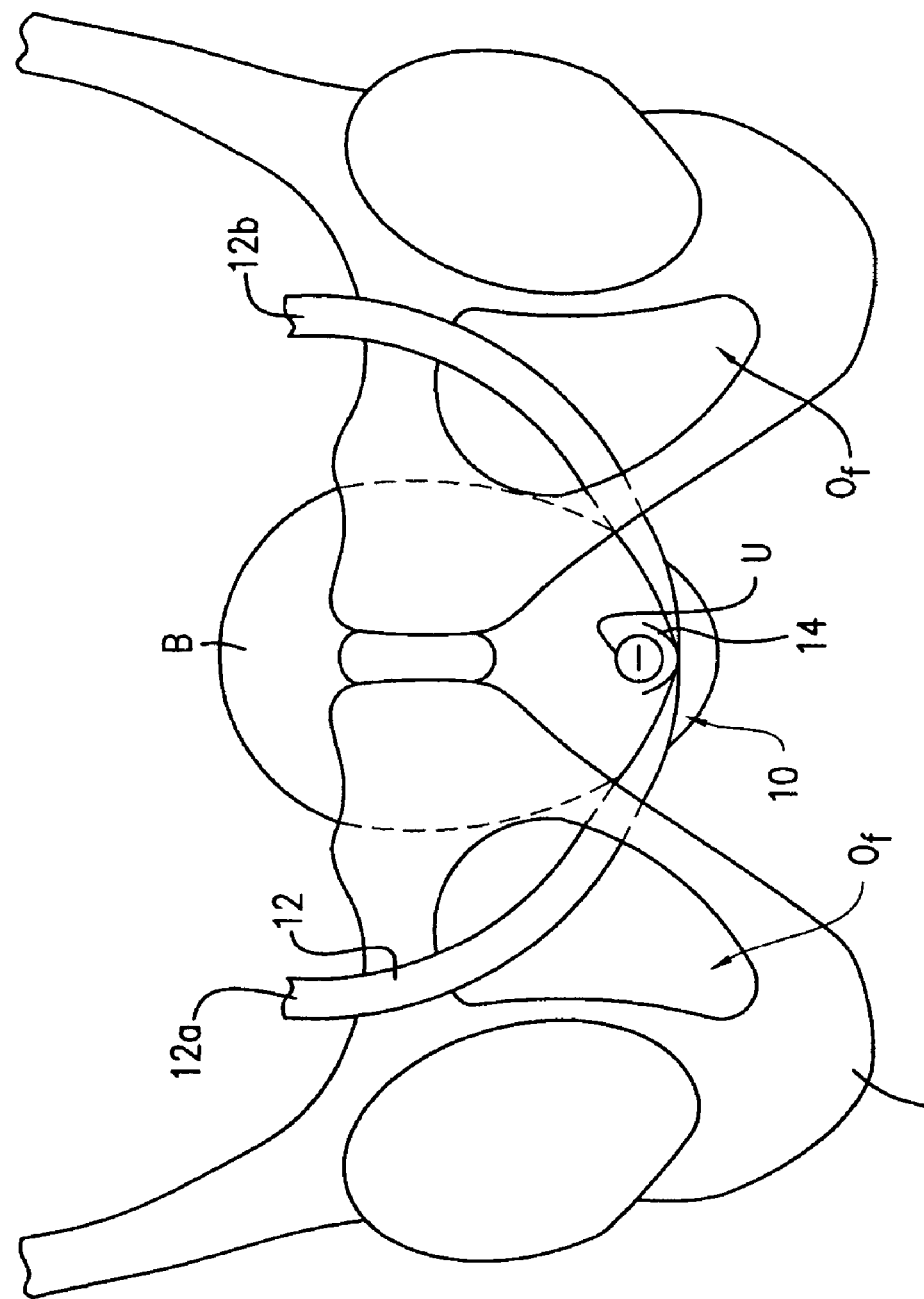
FIG. 6 is a front view of the pelvic bone of a female showing the position of the support tape of the urethra with an obturator passage of the tape.

FIG. 6 illustrates the placement of the tape portion 12 of the urethra support 10 under the urethra U with a trans-obturator passage of tape ends, 12a and 12b.

Figure 7:
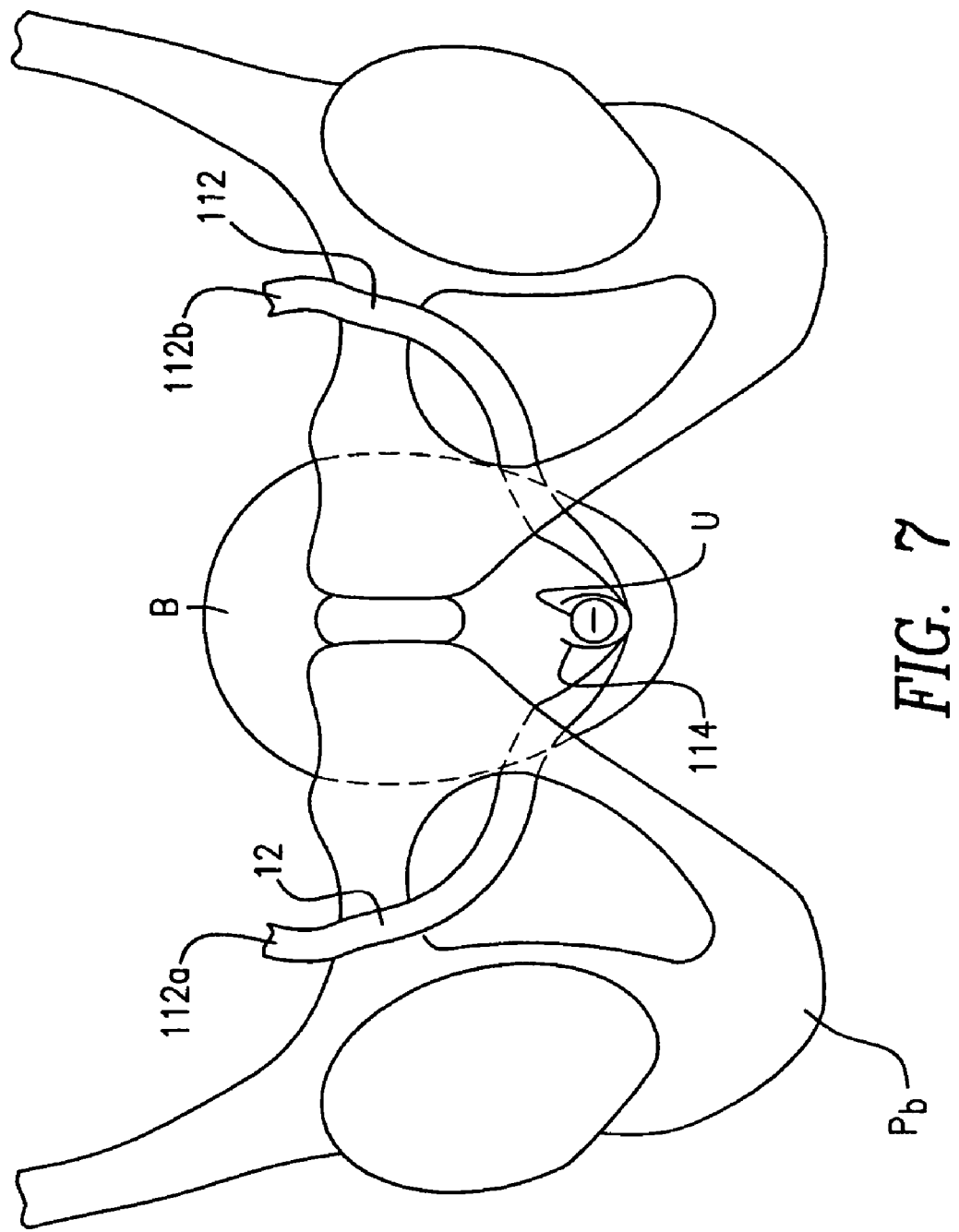
FIG. 7 is a front view of the pelvic bone of a female showing the position of the extensions of the tape as they wrap around the urethra.

FIG. 7 illustrates the placement of the urethra support 10, under the urethra U, with the wing extensions, e.g., 114a wrapping at least partially around the urethra U. While a trans-oburator passage of the tape ends 12a, 12b is shown, the wrapping effect could accompany a retro-pubic passage of the tape ends 12a, 12b.

The extensions 14, 114 extend laterally and posteriorly relative to the urethra U and can curve to wrap around the lateral and anterior aspects of the urethra U. The material from which the tape portion 12 and extension 14 is manufactured induces in-growth of fibroblastic cells which contribute to the eventual formation of scar tissue. Over time, the scar matures and contractile forces within the scar tissue cause a tightening and shrinking of the tissue. These phenomena take place along the full length of the tape portion 12, as well as, within the material of the extension 14. The scar formation and the material of the tape portion 12 and extension 14 create a stiffening around and under the urethra U, which then re-creates the supporting function of the original healthy tissue. Additionally, where the extension 14 is placed laterally to the urethra, support is added there as well. The inclusion of support below, to the sides and above the urethra U imparts a restriction and a compressive force upon the tissue of the urethra U, which increases the urethral sphincter opening pressure, thereby reducing the potential for involuntary urine loss.

It should be understood that the embodiments described herein are merely exemplary and that a person skilled in the art may make many variations and modifications without departing from the spirit and scope of the invention as defined in the appended claims. All such variations and modifications are intended to be included within the scope of the present invention as defined in the appended claims.

I/We claim:

1. A urethra support, comprising:
   an elongated mesh tape portion having a longitudinal axis and first and second opposed longitudinal edges that are substantially parallel to said longitudinal axis;
   a first mesh extension arranged alongside said first longitudinal edge of said tape portion so as to extend along a portion of a length thereof substantially parallel to said longitudinal axis, said first mesh extension extending laterally outwardly from said first longitudinal edge of said tape portion and said first mesh extension having a projecting edge spaced a distance from said first longitudinal edge of said tape portion;
   a second mesh extension arranged alongside said second longitudinal edge of said tape portion so as to extend along a portion of a length thereof substantially parallel to said longitudinal axis, said second mesh extension extending laterally outwardly from said second longitudinal edge of said tape portion and said second mesh extension having a projecting edge spaced a distance from said second longitudinal edge of said tape portion; and
   a shaping element for holding said first mesh extension and said second mesh extension in a position proximate to a urethra of a patient, wherein said shaping element is elastically biased to a predetermined shape.

2. The urethra support of claim 1, wherein said shaping element is Nitinol.

3. The urethra support of claim 1, wherein said shaping element is a heat-treated polymer.

4. The urethra support of claim 1, wherein said shaping element has at least a portion thereof approximating a U-shape.

5. The urethra support of claim 1, wherein said shaping element is deformable and retains a shape after deformation.

6. The urethra support of claim 1, wherein said first mesh extension and said second mesh extension are integral with said tape portion.

7. The urethra support of claim 6, wherein said urethra support is cut from a single piece of material.

8. The urethra support of claim 6, wherein said first mesh extension has a first end section that is separated from said tape portion by a first slit, and said second mesh extension has a second end section that is separated from said tape portion by a second slit.

9. The urethra support of claim 1, wherein said first mesh extension and said second mesh extension are welded to said tape portion.

10. The urethra support of claim 1, wherein said first mesh extension and said second mesh extension are adapted to be wrapped at least partly around the urethra.

11. The urethra support of claim 1, wherein said first mesh extension and said second mesh extension are fabricated from a biocompatible material.

12. The urethra support of claim 10, wherein said first mesh extension and said second mesh extension are fabricated from a material, which promotes tissue in-growth in and around the area under and lateral to the urethra.

13. The urethra support of claim 12, wherein the tissue in-growth promoted by said material contributes to the formation of sear tissue.

14. The urethra support of claim 1, wherein said first mesh extension has a first center section that is affixed to said tape portion along said first longitudinal edge, and said second mesh extension has a second center section that is affixed to said tape portion along said second longitudinal edge.

15. The urethra support of claim 1, wherein said first mesh extension has a first length, said first length being sufficient to wrap said first mesh extension at least partly around the urethra, said second mesh extension has a second length, said second length being sufficient to wrap said second mesh extension at least partly around the urethra, and said tape portion has a third length, said third length being greater than each of said first and second lengths.

16. A urethra support, comprising:
an elongated mesh tape portion having a longitudinal axis and first and second opposed longitudinal edges that are substantially parallel to said longitudinal axis;
a first mesh extension arranged alongside said first longitudinal edge of said tape portion so as to extend along a portion of a length thereof substantially parallel to said longitudinal axis, said first mesh extension extending laterally outwardly from said first longitudinal edge of said tape portion and said first mesh extension having a projecting edge spaced a distance from said first longitudinal edge of said tape portion;
a second mesh extension arranged alongside said second longitudinal edge of said tape portion so as to extend along a portion of a length thereof substantially parallel to said longitudinal axis, said second mesh extension extending laterally outwardly from said second longitudinal edge of said tape portion and said second mesh extension having a projecting edge spaced a distance from said second longitudinal edge of said tape portion; and
a shaping element for holding said first mesh extension and said second mesh extension in a position proximate to a urethra of a patient, wherein said shaping element is at least partially covered by said first mesh extension and said second mesh extension.

17. A urethra support, comprising:
an elongated mesh tape portion having a longitudinal axis and first and second opposed longitudinal edges that are substantially parallel to said longitudinal axis;
a first mesh extension arranged alongside said first longitudinal edge of said tape portion so as to extend along a portion of a length thereof substantially parallel to said longitudinal axis, said first mesh extension extending laterally outwardly from said first longitudinal edge of said tape portion and said first mesh extension having a projecting edge spaced a distance from said first longitudinal edge of said tape portion;
a second mesh extension arranged alongside said second longitudinal edge of said tape portion so as to extend along a portion of a length thereof substantially parallel to said longitudinal axis, said second mesh extension extending laterally outwardly from said second longitudinal edge of said tape portion and said second mesh extension having a projecting edge spaced a distance from said second longitudinal edge of said tape portion; and
a shaping element for holding said first mesh extension and said second mesh extension in a position proximate to a urethra of a patient, wherein said shaping element is at least partially interwoven with said first mesh extension and said second mesh extension.

18. A urethra support, comprising:
an elongated mesh tape portion having a longitudinal axis and first and second opposed longitudinal edges that are substantially parallel to said longitudinal axis;
a first mesh extension arranged alongside said first longitudinal edge of said tape portion so as to extend along a portion of a length thereof substantially parallel to said longitudinal axis, said first mesh extension extending laterally outwardly from said first longitudinal edge of said tape portion and said first mesh extension having a projecting edge spaced a distance from said first longitudinal edge of said tape portion, said first mesh extension having first and second end sections and a first center section intermediate said first and second end sections, said tape portion being affixed to said first center section along said first longitudinal edge so as to extend along a length thereof and substantially parallel to said longitudinal axis, but not affixed to said first and second end sections; and
a second mesh extension arranged alongside said second longitudinal edge of said tape portion so as to extend along a portion of a length thereof substantially parallel to said longitudinal axis, said second mesh extension extending laterally outwardly from said second longitudinal edge of said tape portion and said second mesh extension having a projecting edge spaced a distance from said second longitudinal edge of said tape portion, said second mesh extension having third and fourth end sections and a second center section intermediate said third and fourth end sections, said tape portion being affixed to said second center section along said second longitudinal edge so as to extend along a length thereof and substantially parallel to said longitudinal axis, but not affixed to said third and fourth end sections.

* * * * *